United States Patent [19]

Saylor

[11] Patent Number: 4,482,251
[45] Date of Patent: Nov. 13, 1984

[54] CLINICAL ANALYZER

[75] Inventor: Richard Saylor, Monsey, N.Y.

[73] Assignee: Electro-Nucleonics, Inc., Fairfield, N.J.

[21] Appl. No.: 312,676

[22] Filed: Oct. 19, 1981

[51] Int. Cl.$^3$ ............................................. G01J 3/50
[52] U.S. Cl. .................................. 356/418; 356/414; 364/498
[58] Field of Search ............................ 356/408–411, 356/414, 418, 419, 432–434, 436, 440; 422/63, 65, 67, 68; 364/497–499, 526

[56] References Cited

U.S. PATENT DOCUMENTS

| Re. 28,803 | 5/1976  | Durkos et al.   | 364/498 X |
|------------|---------|-----------------|-----------|
| 3,580,683  | 5/1971  | Schulkind       | 356/414   |
| 3,703,336  | 11/1972 | Rosse et al.    | 422/67 X  |
| 3,783,300  | 1/1974  | Johnson         | 356/434 X |
| 3,960,497  | 6/1976  | Acord           | 422/67    |
| 4,053,235  | 10/1977 | Hampton et al.  | 356/418   |

FOREIGN PATENT DOCUMENTS

| 42188 | 4/1977 | Japan | 356/414 |
| 60692 | 5/1977 | Japan | 422/67  |

Primary Examiner—F. L. Evans
Attorney, Agent, or Firm—Robert Scobey

[57] ABSTRACT

A clinical analyzer that is microprocessor controlled is disclosed. A shuttle carries a plurality of cuvettes containing liquids to be spectrophotometrically analyzed by a single beam spectrophotometer. The shuttle moves the cuvettes past the spectrophotometer in a plurality of cycles to complete a given test. At the beginning of a test, spectrophotometer lamp energization is controlled to achieve a predetermined spectrophotometer output for a reference filter. The remaining filters are then positioned one-by-one, and amplifier gain is adjusted to achieve optimum spectrophotometer output for each filter. The gain associated with each filter is stored by the microprocessor, and thereafter during the test, when each filter is used, the stored gain associated with that microprocessor is utilized in the amplifier circuitry. Additionally, at the beginning of each cycle of shuttle movement, an air calibration reading is taken, to be used by the microprocessor in determining absorbance. This air-only reading, in combination with a reference reading taken with a water-filled cuvette at any convenient time, serves to provide for accurate calibration of the system, overcoming problems of drift.

12 Claims, 7 Drawing Figures

CLINICAL ANALYZER

BACKGROUND AND BRIEF DESCRIPTION OF THE INVENTION

This invention relates to clinical analyzers. More particularly, a microprocessor-controlled spectrophotometric analyzing system is provided which incorporates unique calibration procedures to provide for highly accurate and dependable readings in a system which is relatively simple. The accurate calibration would be expected to be present only in systems much more expensive and much more complicated, and particularly those utilizing dual beam spectrophotometry.

It is known to analyze liquid-filled cuvettes spectrophotometrically to carry out clinical analyses. Many systems are on the market, and many are extremely complex in the handling of the cuvettes during testing. The present invention utilizes a shuttle which carries a number of cuvettes and which is moved by a stepper motor back and forth in a plurality of cycles past a single beam spectrophotometer. A microcomputer is utilized for all process control, namely, shuttle movement, filter wheel movement, calibration procedures, and control of all other process parameters.

In the past, single beam spectrophotometers have been subject to calibration difficulties due to circuit drift. Calibration problems are overcome in the present invention by utilizing unique calibration procedures so that calibration is always tightly controlled. In particular, energization of the lamp in the spectrophotometer is controlled, and lamp output is monitored to achieve optimum signal output and correct calibration. Additionally, the various filters employed in the spectrophotometer are frequently interrogated, and amplifier gain is adjusted for each filter to achieve optimum signal output. The gain for each filter is stored in the microprocessor and thereafter used for a test.

Additionally, a water-filled cuvette reference reading is taken whenever convenient, and is used in conjunction with air-only readings taken by the system often and at convenient times to provide for higly controlled, accurate, and frequent calibration of the circuitry.

The invention thus is broadly involved with process control, and specifically with process control in a clinical analyzer.

The invention will be more completely understood by reference to the following detailed description of a representative, but presently preferred embodiment thereof.

DETAILED DESCRIPTION

Figure 1:
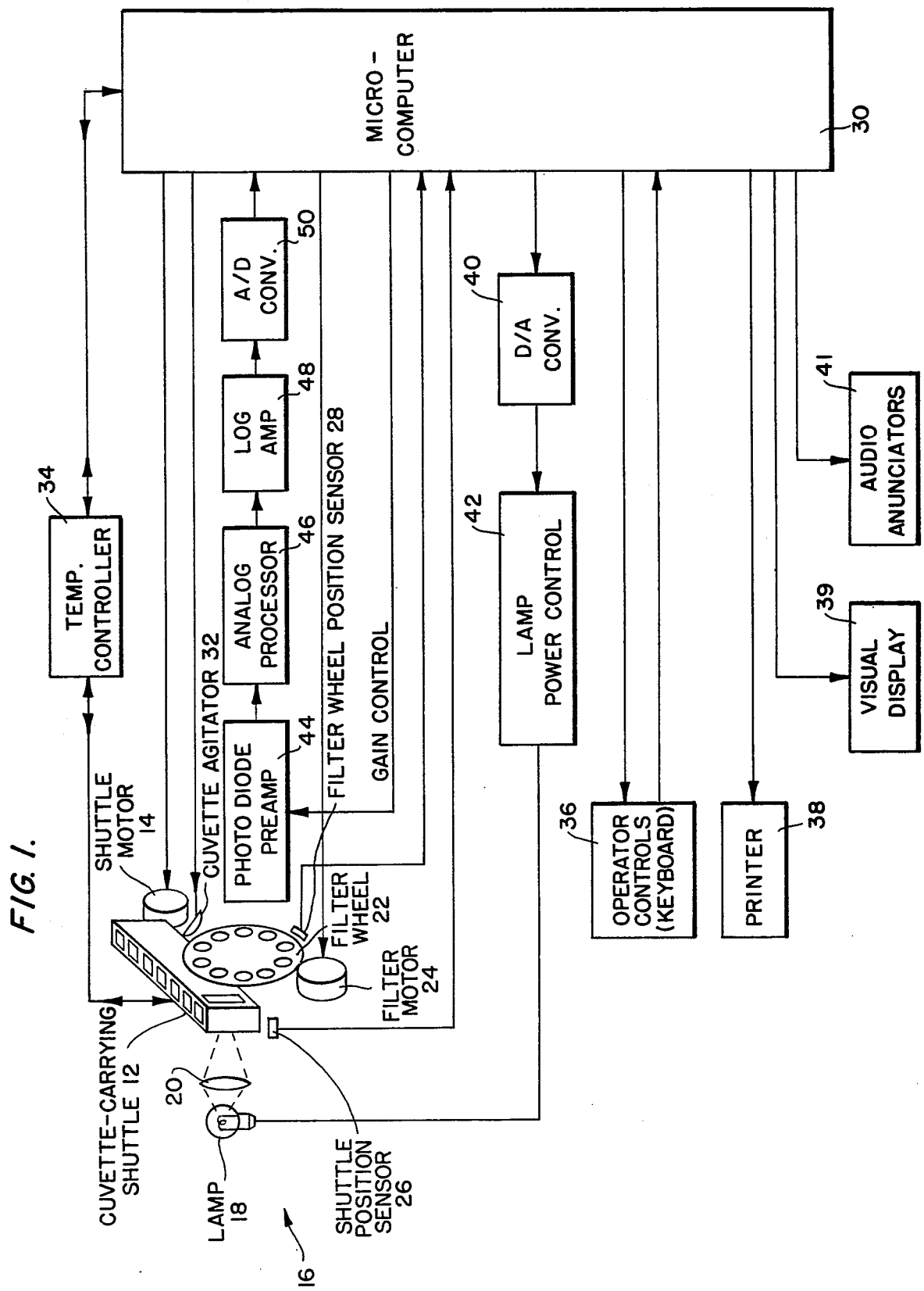
FIG. 1 is a block diagram of a system in accordance with the invention.

Referring to FIG. 1, an overall system embodying the invention is shown. That system includes a cuvette-carrying shuttle 12 which is driven by a shuttle motor 14 to move past a spectrophotometer assembly 16 comprising a lamp 18, lens assembly 20 and filter wheel 22, driven by a filter motor 24. Advantageously, both the shuttle motor 14 and the filter motor 24 are stepper motors, so that control of the movement of the shuttle and filter wheel may be easily achieved. In particular, a shuttle position sensor 26 and a filter wheel position sensor 28 are included whhich sense and provide appropriate signals when the shuttle and filter wheel are in reference or "home" positions. These signals are applied to a microcomputer 30 which is responsible for control of the entire system.

The microcomputer 30 supplies control and energizing signals to the shuttle motor 14, the filter motor 28, as well as to a cuvette agitator 32 which provides for agitation of a cuvette to stir the contents therein during a test, and to a temperature controller 34 for the purposes of control of the temperature of the liquids within the cuvettes. Additionally, the microcomputer receives signals from and transmits signals to an operator controls device 36, e.g., the keyboard, as well as signals to a printer 38 which prints the results of the spectrophotometric analyses that are conducted by the system. Additionally, the microcomputer 30 controls the energization of the lamp 18, via a digital to analogue converter 40 and a lamp power control 42. Typically, lamp control is carried out once during a test of a group of cuvettes. Additionally, the microcomputer provides a gain control signal to a photo diode preamplifier 44 which receives signals from the photo diode in the spectrophotometer. Gain control, in combination with lamp power control, provides for highly accurate signal processing.

Signals from the preamplifier 44 are applied to an analogue processor 46 and thence through a log amplifier 48 and analogue to digital converter 50, from which they are applied to the microcomputer 30 for processing in the system and printout of test results.

The system of FIG. 1 also includes appropriate visual display 39 and audio annunciators 41 which provide suitable visual and audio output to the operator of the system.

The system operates to move the cuvette-filled shuttle 12 back and forth past the spectrophotometer 16 in a number of cycles during a given test. During each "cycle", one or more of the cuvettes is interrogated. Cuvette readings are taken during each cycle to provide kinetic and end point data. The microcomputer 30, under control of the operator, may provide for "batch" or "profile" testing of all cuvettes. In other words, for a "batch" test, all cuvettes undergo the same chemical reaction, and the same test procedure is carried out for each cuvette. In a "profile" test, blood serum typically from a single patient fills the various cuvettes, and a different test is conducted on each cuvette. The operator of the system controls the procedure by suitable keyboard data entry, and different batch and profile tests may be programmed by the user.

At the beginning of a test procedure, during incubation, when the shuttle is in its reference or "home" position, gain adjustments are made and stored for subsequent use during testing for each filter in the filter wheel 22 of the spectrophotometer. Additionally, an air reading is taken for instrument calibration, to determine the slope and Y-axis intercept of a calibration curve.

During a test run, each time the shuttle returns to its reference or "home" position, an air reading is taken to redetermine the Y-axis intercept of the calibration curve of the instrumentation at the time of actual test. The shuttle returns to that home position many times during a test, i.e., once during each cycle of shuttle movement, and hence frequent Y-axis intercept redeterminations are made by the system, overcoming the major problem of lamp output variations which directly affect the Y-axis intercept. Slope variations, caused by drift of other circuit parameters, occur much more slowly, and hence require adjustment less frequently, e.g., once during a test run.

The details of the system are given below.

Figure 2:
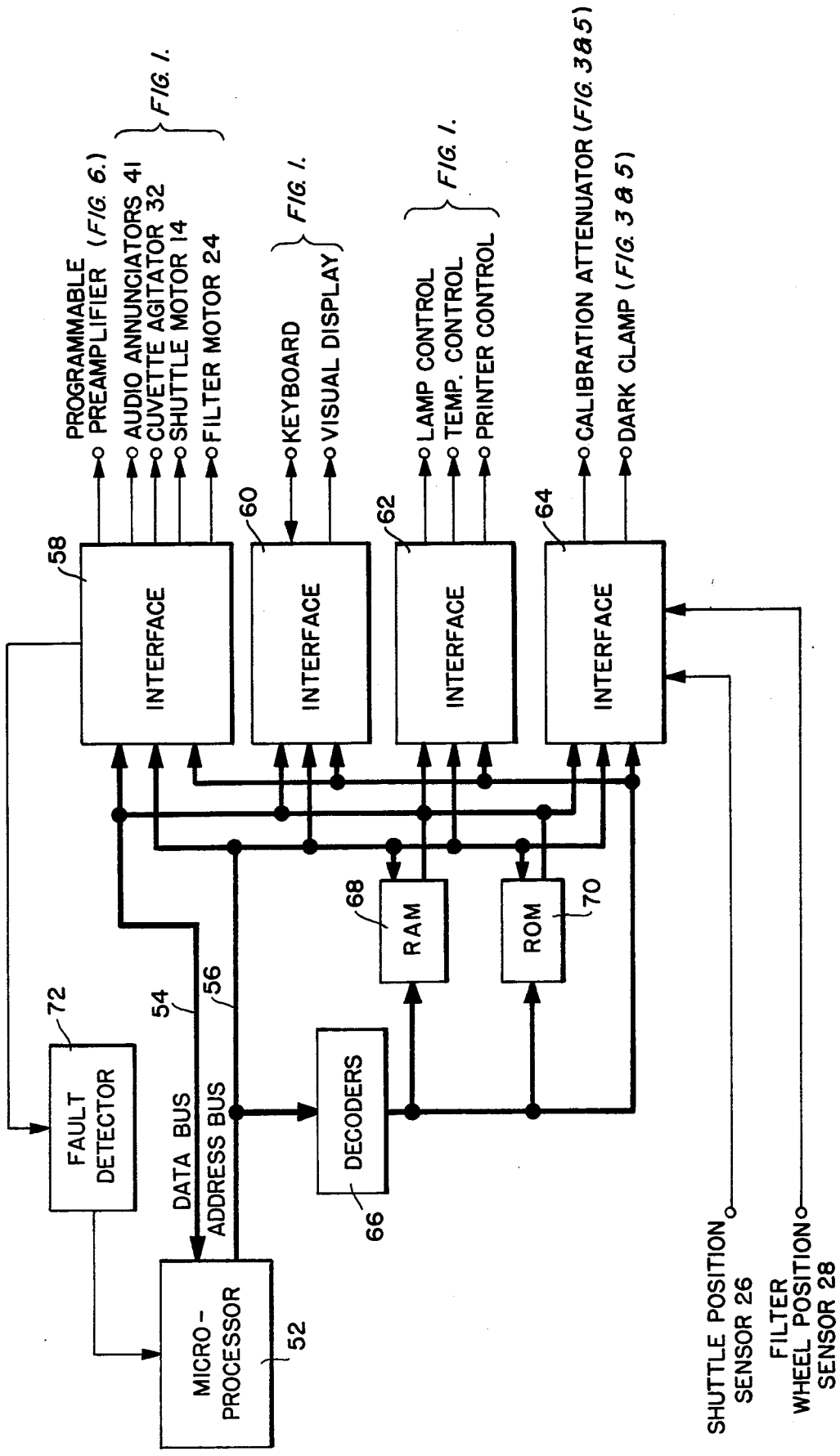
FIG. 2 is a block diagram of a part of the system of FIG. 1.
Figure 6:
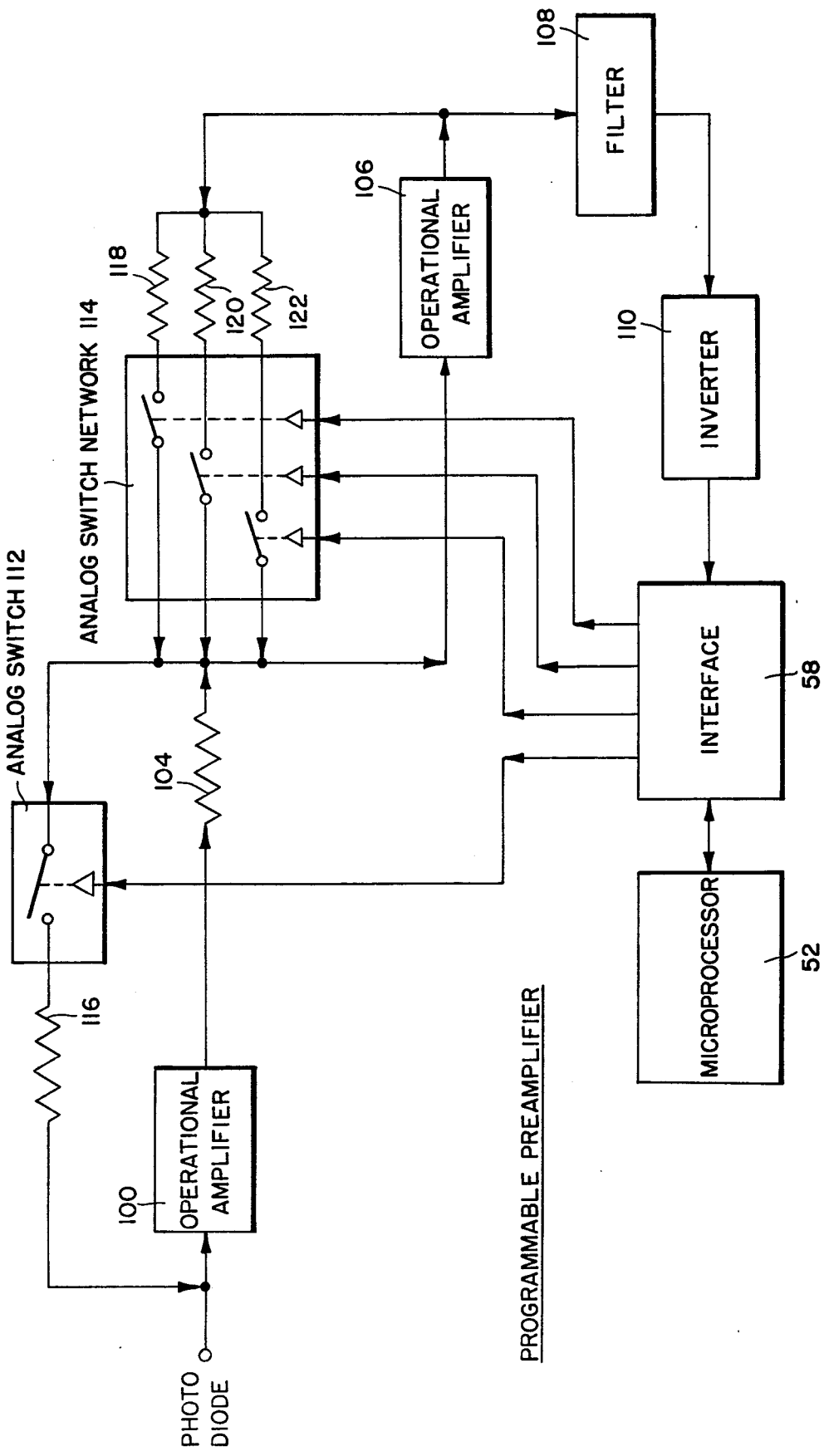
FIG. 6 is a circuit diagram, mainly in block diagram form, of a programmable preamplifier useful in the invention.

FIG. 2 gives the details of the microcomputer 30. The system includes a microprocessor 52, which may be an Intel microprocessor Model 8085, to give an example. The microprocessor 52 communicates via a data bus 54 and an address bus 56 with interfaces 58, 60, 62 and 64, as well as with decoders 66 and random access memory (RAM) and read only memory (ROM) units 68 and 70. The interfaces 58 to 64 provide appropriate interfacing between the microprocessor 52 and the various input/output devices, as indicated in FIG. 2. Thus, the interface 58 communicates with a programmable preamplifier, which is shown in FIG. 6 to be described in more detail below. Additionally, that interface communicates with audio annunciators 41, cuvette agitator 32, shuttle motor 14, and filter motor 24, all of FIG. 1. Additionally, that interface communicates with a fault detector 72 coupled to the microprocessor 52, so that, if at any time a fault is detected in the system, the microprocessor is suitably activated to provide appropriate indication to the system operator, to carry out resetting functions and similar fault procedures, as necessary.

Under the control of the interface 58, the shuttle motor 14, which is the stepping motor, causes the shuttle 12 to move back and forth in linear fashion. Typically, that shuttle might be expected to carry 12 cuvettes, which are loaded with liquid for analysis by the spectrophotometer 16. Once the shuttle 12 is detected as being in its reference or "home" position, by a suitable signal from the shuttle position sensor 26, further movement of the shuttle is detected and controlled by counting shuttle motor cycles of energization, since for each energization of the shuttle motor, which is a stepping motor, the shuttle 12 moves a predetermined distance. Thus it is not necessary to monitor the position of the cuvette-carrying shuttle 12 except at its reference or "home" position. This greatly simplifies system operation and control. Likewise, the position of the filter wheel 22 as controlled by the filter motor 24, is easily governed, since the filter motor is also a stepping motor, and the reference or "home" position of that filter wheel is determined by a suitable signal from the filter wheel position sensor 28. Both of the sensors 26 and 28 provide inputs to the interface 64, as noted in FIG. 2. The other interfaces of FIG. 2 control system elements, as noted.

Cuvette agitator 32, which is controlled by the interface 58, may advantageously comprise a rotary solenoid controlled lever which strikes a particular cuvette whose contents are to be agitated.

Figure 3:
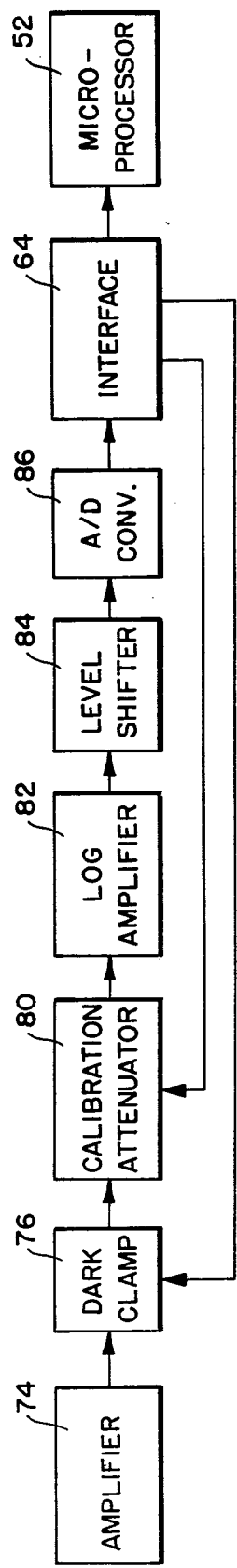
FIG. 3 is a block diagram of a part of the system of FIG. 1.

FIG. 3 gives the details of that part of the operating system dealing with signal processing of the signals from the spectrophotometer 16. The system includes an amplifier 74 which supplies signals to a dark clamp 76, the details of which are given in FIG. 4, to be described below in more detail. The dark clamp 76 serves to provide dark-level restoration. In particular, under the control of the microprocessor 52, during any particular testing procedure, the shuttle motor 14 drives the shuttle 12 so that the opaque area of the shuttle immediately adjacent to the cuvette next-to-be interrogated blocks the beam of light from the lamp 18. In this position of the shuttle 12, with no light reaching the photo diode preamplifier 44 of FIG. 1, the signal from the amplifier 74 represents zero transmittance or total absorbance.

Figure 4:
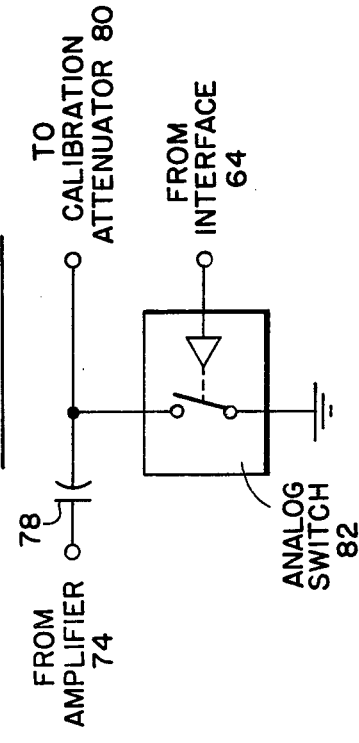

To make sure that the "dark" signal is correct, the dark clamp circuit of FIG. 4 is utilized. Quite simply, the signal from the amplifier 74 passes through a capacitor 78 on its way to calibration attenuator 80. An analogue switch 82 is included, under the control of interface 64 of FIG. 2. Selectively, the analogue switch is activated to ground the capacitor 78. This grounding action occurs under microprocessor control when the shuttle 12 is halted, as described above, immediately adjacent to a cuvette to be interrogated. During the time that the light from the lamp 18 is blocked totally, the analogue switch 82 is activated to ground the capacitor 78. Once that capacitor is charged, the analogue switch 82 is opened, and then the shuttle 12 is moved to the adjacent cuvette to be interrogated by the spectrophotometer. Since the resulting voltage change at the capacitor 78 commences from ground level, it is a true zero-based signal.

Figure 5:
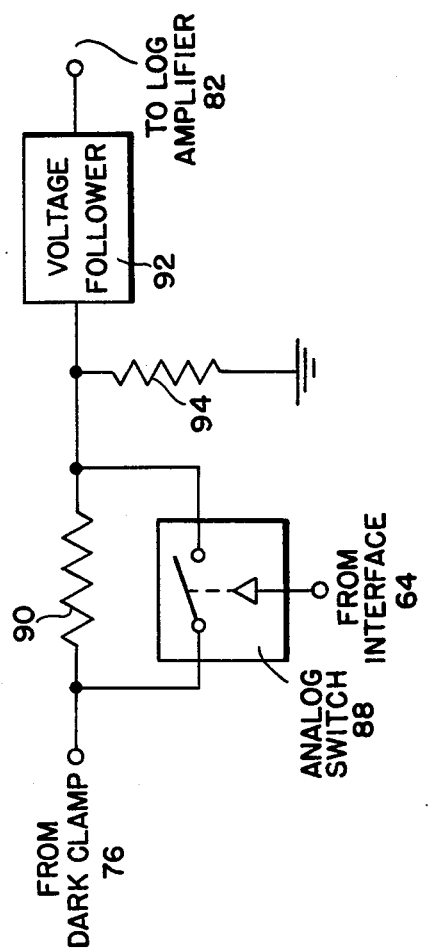
FIGS. 4 and 5 are circuit diagrams, partly in block diagram form, of part of the circuit of FIG. 3.

Returning to FIG. 3, the signal from the dark clamp circuit 76 is applied through a calibration attenuator 80, which is shown in FIG. 5, and which will be described in more detail below. Briefly, attenuation of the signal is provided for calibration purposes. Otherwise, the signal passes un-attenuated to a log amplifier 82 which converts the transmittance signal to an absorbence signal utilizing the equation:

$$e_o = -2(2 + \log_{10} t) \tag{1}$$

where t is the transmittance.

The signal from the log amplifier 82 is applied to a level shifter 84, and appropriate scaling and level shifting take place so that the output signal from the level shifter follows the equation:

$$e_o = 10A \tag{2}$$

Equation (2) above is derived from equation (1) by recognizing that the definition of optical absorbance is:

$$A = -\log_{10} t \tag{3}$$

Substituting from equation 3 into equation 1 produces the following equation:

$$e_o = -4 + 2A \tag{4}$$

which by virtue of the scaling and level shift taking place in the level shifter 84 produces a signal that follows equation (2).

The signal from the level shifter 84 is converted to a digital value (typically 12 bit) by an analogue to digital converter 86. The signal from that converter is applied to the interface 64, which communicates with the microprocessor 52.

The calibration attenuator 80 of FIG. 3 is shown in detail in FIG. 5. During calibration times, it is desired to selectively attenuate the spectrophotometric signal. The reasons for the attenuation will be given in more detail below. In any event, the signal from the dark clamp 76 is applied normally directly (without attenuation) through an analogue switch 88 to voltage follower 92 and thence to log amplifier 82 of FIG. 3. The analogue switch 88 is under the control of the interface 64 of FIG. 2. When it is desired to calibrate the circuit, the interface 64 causes the analogue switch 88 to change from its normally closed condition to an open condition, in which resistor 90 is no longer shunted by the analogue switch. Thus the signal from the dark clamp 76 is attenuated, by the action of resistor 90 in conjunction with resistor 94 connected to ground. Typically, the resistor 90 might be approximately 324K ohms, while the resistor 94 may be 10K ohms. This ratio of resistances gives an attenuation of 3%, which represents an optical absorbence of 1.52 absorbence units. This particular value of optical absorbence is arbitrary, and any convenient number may be selected for the purpose of calibration. The value is stored by the microprocessor 52 and is used as a calibration factor for time and temperature variation particularly in the log amplifier 82, in the analogue to digital converter 86, and in associated circuits.

Figure 7:
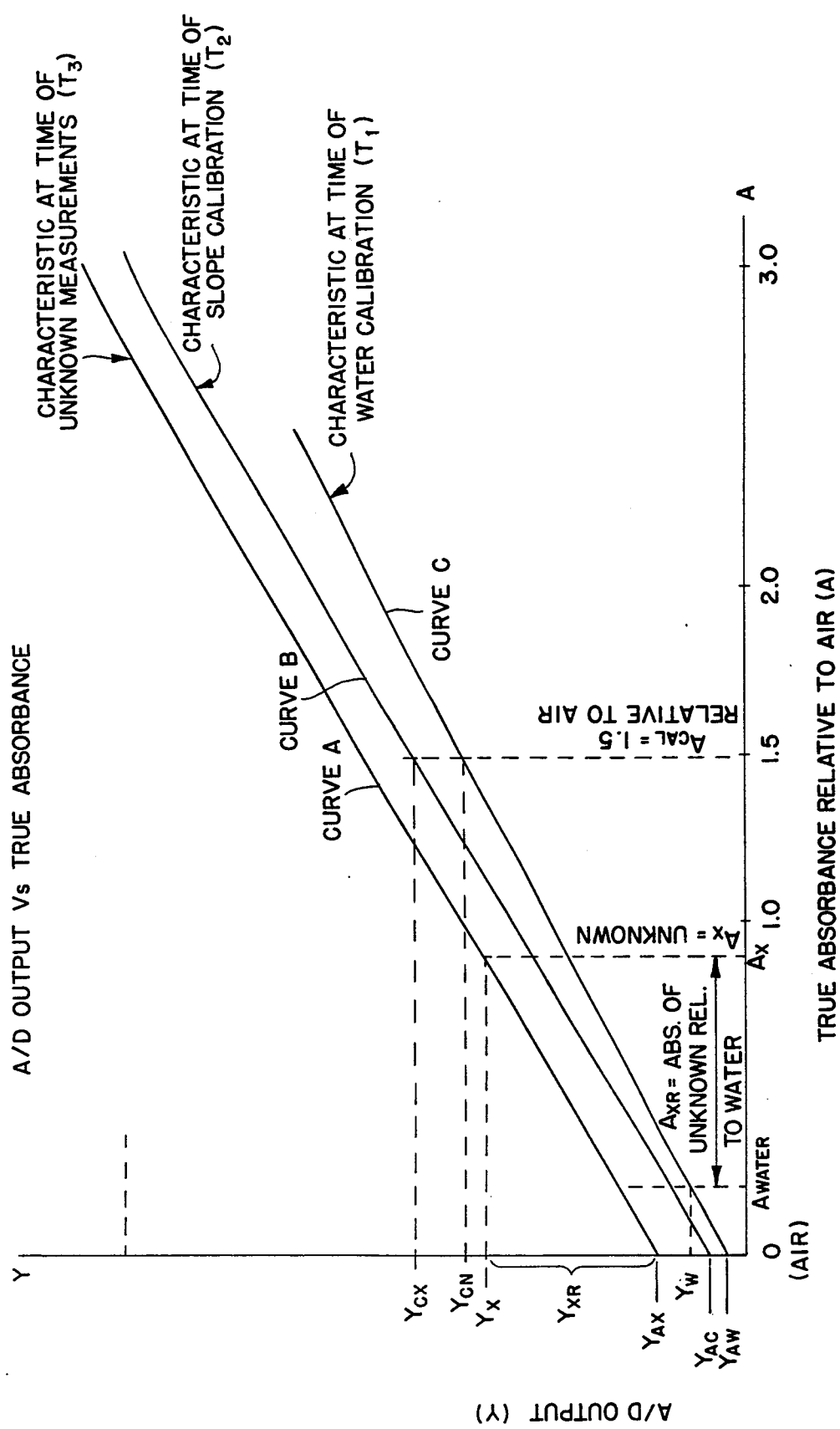
FIG. 7 is a series of characteristic curves plotting output versus true absorbence, useful in understanding the invention.

The reason for utilizing a calibration attenuator circuit 80 will be appreciated by reference to the characteristic curves of FIG. 7. Curve A represents the characteristic response of the system at the time of the actual measurement of a cuvette under interrogation. Curve A is a theoretical curve, since, at the time of interrogation, testing and not calibration is occurring. Curve B is a curve which is developed and is a true calibration curve, as is curve C. Curve B represents an air-only calibration, which takes place at the beginning of each test run. Typically, each test run, constituting a number of cycles of back and forth movement of the shuttle, may encompass a 2–10 minute period, while each cycle may take no more than 15 seconds, e.g. At the beginning of a test run, the shuttle 12 is in its reference or "home" position. In this position, nothing blocks the flow of light from the lamp 18 to the photo diode preamplifier 44, and hence an "air-only" reading may be taken in the system, in which light passes only through one of the filters in the filter wheel 22. The system scale factor may thus be set for this 100% transmittance condition. The adjustment is done at any wavelength, since it is valid for all wavelengths, and hence any filter among the group of filters in the wheel 22 may be employed. Two readings are taken, one with the analogue switch 88 of FIG. 5 open, to produce the value $Y_{cx}$ of curve B in FIG. 7. The other reading is taken with the analogue switch 88 closed, so that no attenuation takes place. This is the reading $Y_{ac}$ of the curve B at the zero absorbance or air condition. This curve B is generated, and its characteristics are stored by the microprocessor 52.

For the purpose of testing, it is assumed that the curve B is parallel to the unknown and desired curve A. Curve C in FIG. 7 is also utilized, representing a "clear" cuvette (typically water-filled), and this curve is developed at anytime convenient during a testing procedure. Curve C need not be re-generated during each test, but is valid over any number of tests, and is dependent upon the optical characteristics of the cuvettes being employed rather than the constants of the control system. Thus, so long as the cuvettes do not change in optical characteristics (so long as tests are conducted with generally a uniform batch of cuvettes), there is no need to regenerate the curve C, since the computed value of absorbance, $A_{water}$, is a constant.

The curve C is generated by utilizing a water-filled cuvette, and again the readings at 1.5 absorbence and zero absorbence are utilized to generate the curve, which is also assumed to be a straight line. The calibration attenuator circuit 80 of FIG. 5 may be utilized to generate these signals representing these absorbances, in the same manner as outlined above for the development of the "air-only" curve B.

The following equation describes the ultimate relationship used by the system:

$$A_{XR} = A_X - A_W \tag{5}$$

where $A_{XR}$ is the absorbance of an unknown specimen under test relative to water, $A_X$ is the measured absorbance of the unknown specimen (corresponding to a signal $Y_X$), and $A_W$ is the cuvette absorbance, as determined by a measurement of a water-filled cuvette determined during the water-calibration step outlined above.

From the curves of FIG. 7, the following is apparent:

$$Y_{XR} = Y_X - Y_{AX} = \Delta Y \text{ of curve A} \tag{6}$$

$$Y_{CR} = Y_{CX} - Y_{AC} = \Delta Y \text{ of curve B} \tag{7}$$

$$Y_{CWR} = Y_{CW} - Y_{AW} = \Delta Y_1 \text{ of curve C} \tag{8}$$

$$Y_{WR} = Y_W - Y_{AW} = \Delta Y_2 \text{ of curve C} \tag{9}$$

Inverse slope of curve
$$A = A_X/Y_{XR} = 1.5/Y_{CR} = \text{inverse slope of curve B} \tag{10}$$

Rearranging equation (9): $A_X = 1.5\ Y_{XR}/Y_{CR}$ \hfill (11)

Inverse slope of curve $C = A_W/Y_{WR} = 1.5/Y_{CWR}$ \hfill (12)

Rearranging equation (11): $A_W = 1.5\ Y_{WR}/Y_{CWR}$ \hfill (13)

Substituting equations (11) and (13) into equation (5) produces:

$$A_{XR} = (1.5\ Y_{XR}/Y_{CR}) - (1.5\ Y_{WR}/Y_{CWR}) \tag{14}$$

The system carries out the computations of equation (14) to determine the absorbance of the specimen under test relative to water.

All of the curves of FIG. 7 follow the form:

$$Y = aX + b \tag{15}$$

where Y represents the output of the analogue to digital converter 50 in FIG. 1, the factor a is the slope of the curve, and b is the Y-axis intercept. The system recognizes that there is a family of curves B (FIG. 7), one for each filter, the curves having the same slope but varying Y-axis intercepts.

The slope is determined at the beginning of each test run, and that slope is applied to all subsequent measurements during the test run in the computational procedures. The slope of the curve is affected by circuit component drift, which takes place slowly over time, and hence one slope determination per test run is sufficient. Y-axis intercept measurements, however, are made much more frequently, since lamp output directly affects the Y-axis intercept. Hence Y-axis intercepts are determined once each cycle of shuttle movement, e.g., at least once every 2-15 seconds. Again, it is assumed that it is not necessary to complete more frequent determination of the Y-axis intercept.

The present system thus proceeds on the basis that curve slope and intercept (FIG. 7) necessary for calibration purposes, is generated as frequently as is reasonable given the constraint of providing rapid testing. While it would be possible to generate a curve B before each and every test of a cuvette, that is not believed to be necessary. Thus, the curve B is generated once at the start of each run or test constituting a plurality of cyles of shuttle movement.

Setting of the scale factor or slope should hold during subsequent movement of the shuttle during the test which, as noted above, is typically a 2 to 10 minute period.

As noted above, other calibrations are carried out by the microcomputer 30. In particular, the energization of the lamp 18 of the spectrophotometer is controlled via digital to analogue converter 40 and lamp power control unit 42 to account for lamp drift. Typically, at the beginning of a test, during the incubation period which the shuttle 12 remains at rest for a relatively long period of time, the microcomputer 30 energizes the lamp 18 with a reference filter in the filter wheel 22 filtering light from the lamp 18. During this time the signal from the system is adjusted so that it is at an optimum level. Thereafter, the filter motor 24 is energized to move the filter wheel in step fashion so that each of the filters on the wheel is successively moved to filter the light from the lamp 18. When each filter is in position, the signal from the photo diode preamp is adjusted by the circuit of FIG. 6 so that it is at an optimum level which is then stored by the microprocessor 52. Referring now to FIG. 6, the signal from the photo diode of the system is applied to an operational amplifier 100. The signal from the amplifier 100 passes via conductor 102 and resistor 104 to an operational amplifier 106. The signal from the operational amplifier 106 passes through a filter 108 and an inverter 110 to interface 58 which is coupled in turn to microprocessor 52. Selective gain is provided by way of analogue switch 112 and analogue switch network 114. The switch 112 is provided for coarse gain control, while the network 114 is used for fine gain control.

To explain, the analogue switch 112 is coupled to the amplifier 100 by a resistor 116. When the analogue switch 112 is closed, the resistor 116 is coupled as a feedback element back to the input of the amplifier 100, varying the gain of that amplifier. Likewise, when any one or more of the analogue switches within the analogue switch network 114 is closed, one or more of resistors 118, 120, and 122 is connected between the output and the input of the operational amplifier 106, varying the gain of that amplifier. Thus, there are four resistors 116 to 122, providing a maximum of 16 different resistor combinations, all of which vary the gain of the system and hence the level of the photo diode signal as it is applied to the filter 108 and ultimately through the interface to the microprocessor 52.

Thus, as each filter element in the filter wheel 22 filters light from the lamp 18, the microprocessor 52 adjusts the gain, by appropriate energization or deenergization of the analogue switches 112 and 114, so that the signal from the system for that particular filter element is at an optimum level. The setting of the analogue switches is stored within the microprocessor 52 so that, later during an actual test procedure when a particular filter element is filtering light passing through a cuvette under test, the gain setting is appropriate to that filter element and is the same as the setting during the optimizing calibration procedure just described.

As indicated above, this gain adjustment procedure may take place at the beginning of a test procedure, when the shuttle 12 is remaining at its reference or "home" position for relatively a long period of time.

Thus, relatively long-term control is achieved by control of the energizing potential of the lamp 18, while short-term control, each time that a filter element is moved into position for active use, takes place during each test cycle.

It will be appreciated that preferred embodiments of the invention have been described above, and that such embodiments are subject to modification. Accordingly, the invention should be taken to be defined by the following claims.

I claim:

1. In a clinical analyzer that includes a shuttle carrying a plurality of cuvettes containing liquid to be analyzed spectrophotometrically by a single beam spectrophotometer including a plurality of light filters, means for moving the shuttle past the spectrophotometer so that selected ones of said cuvettes are examined in a plurality of cycles of movement of each cuvette past the spectrophotometer to complete a test run, the improvement for calibrating the spectrophotometer circuitry comprising means for periodically completing a spectrophotometric reading of air only, including an attenuation circuit providing for varying signal attenuation to produce two air-only readings that together determine the slope of a calibration curve, and means for selectively activating said attenuation circuit.

2. A signal analyzer according to claim 1, in which said predetermined attenuation is generally about 3% representing an optical absorbance of about 1.5 absorbance units.

3. A clinical analyzer as in claim 1, in which said activating means activates said attenuation circuit at least once during said plurality of cycles.

4. A clinical analyzer as in claim 3, including a gain control and means active at least at the beginning of a test for completing a reference spectrophotometric reading of each of a plurality of said filters and adjusting said gain control for each filter to achieve a preselected spectrophotometric output, means for storing said gain adjustment for each filter, and means active thereafter during each cycle of testing during said test for adjusting said gain control so that it conforms to the value stored for a given filter when the filter is employed during said test.

5. A clinical analyzer according to claim 4, in which said gain control adjustment means comprises a plurality of analogue switches, various combinations of which are activated to provide for gain adjustment.

6. A clinical analyzer according to claim 5, in which said gain storing and gain adjustment means comprises a microprocessor for storing signals representing said various combinations of said analogue switches providing for said gain adjustment, and interface means coupled to said microprocessor and activating said analogue switches to produce said various combinations during a test.

7. A clinical analyzer as in claim 5, including means for completing a spectrophotometric reading of a cuvette to obtain a reading of a "clear" cuvette for reference purposes.

8. In a clinical analyzer that includes a shuttle carrying a plurality of cuvettes containing liquids to be analyzed past a spectrophotometer, said spectrophotometer having gain control and including a lamp and a filter assembly containing a plurality of light filters, and means for moving the shuttle past the spectrophotometer so that selected ones of said cuvettes are examined in a plurality of cycles of movement of each cuvette past the spectrophotometer so that a plurality of said cycles complete a test for a group of said cuvettes, the improvement for adaptively calibrating the spectrophotometer circuitry comprising means active at least at the beginning of each test for completing a reference spectrophotometric reading of each of a plurality of said filters and adjusting said gain control for each filter to achieve a preselected spectrophotometric output, means for storing said gain adjustment for each filter, and means active thereafter during each cycle of testing during said test for adjusting said gain control so that it conforms to the value stored for a given filter when that filter is employed during said test.

9. A clinical analyzer as in claim 8, in which said adjustment means includes means for first completing a reference spectrophotometric reading of a reference filter and adjusting the energization of said lamp to achieve a predetermined spectrophotometric output, and thereafter completing said spectrophotometric reading of said filters for said gain control adjustment.

10. A clinical analyzer according to claim 8, in which said gain control adjustment means comprises a plurality of analogue switches, various combinations of which are activated to provide for gain adjustment.

11. A clinical analyzer according to claim 10, in which said gain storing and gain adjustment means comprises a microprocessor for storing signals representing said various combinations of said analogue switches providing for said gain adjustment, and interface means coupled to said microprocessor and activating said analogue switches to produce said various combinations during a test.

12. In a system for process monitoring utilizing a source for engergizing a test instrument and detection circuitry coupled to the test instrument and including gain control in a plurality of test modalities, the improvement for adaptively calibrating said system comprising means periodically activated for controlling the energization of said source to an extent so that a predetermined output is achieved by said detection circuitry, means activating each of said modalities when said source is energized to said extent and adjusting said gain control so that the output of said detection circuitry achieves a preselected value, means for storing said gain adjustment for each of said modalities, and means active thereafter during process monitoring for adjusting said gain control to the value stored for a given modality when that modality is employed during process monitoring.

* * * * *